(12) United States Patent
McIntosh et al.

(10) Patent No.: US 8,088,099 B2
(45) Date of Patent: Jan. 3, 2012

(54) FLUID DISPENSER

(75) Inventors: Kevin D. McIntosh, Brooklyn Park, MN (US); Victor D. Dolecek, Centennial, CO (US)

(73) Assignee: Arteriocyte Medical Systems, Inc., Cleveland, OH (US)

( * ) Notice: Subject to any disclaimer, the term of this patent is extended or adjusted under 35 U.S.C. 154(b) by 0 days.

(21) Appl. No.: 12/592,435

(22) Filed: Nov. 23, 2009

(65) Prior Publication Data

US 2010/0076399 A1    Mar. 25, 2010

(51) Int. Cl.
*A61M 37/00* (2006.01)
(52) U.S. Cl. .......................................... 604/82
(58) Field of Classification Search ............... 604/82, 604/191; 222/137
See application file for complete search history.

(56) References Cited

U.S. PATENT DOCUMENTS

| | | | | |
|---|---|---|---|---|
| 2,112,160 A | | 3/1938 | Johnson | 128/234 |
| 3,223,083 A | | 12/1965 | Cobey | 128/92 |
| 3,467,096 A | | 9/1969 | Horn | 128/218 |
| 3,767,085 A | * | 10/1973 | Cannon et al. | 222/82 |
| 3,828,980 A | * | 8/1974 | Creighton et al. | 222/137 |
| 4,040,420 A | | 8/1977 | Speer | 128/218 |
| 4,090,129 A | * | 5/1978 | Gear | 324/71.1 |
| 4,109,653 A | | 8/1978 | Kozam et al. | 128/218 |
| 4,121,739 A | * | 10/1978 | Devaney et al. | 222/137 |
| 4,359,049 A | | 11/1982 | Redl et al. | 128/218 |
| 4,367,737 A | * | 1/1983 | Kozam et al. | 604/191 |
| 4,471,765 A | * | 9/1984 | Strauss et al. | 600/5 |
| 4,609,371 A | | 9/1986 | Pizzino | 604/191 |
| 4,631,055 A | | 12/1986 | Redl et al. | 604/82 |
| 4,735,616 A | | 4/1988 | Eibl et al. | 604/191 |
| 4,753,536 A | * | 6/1988 | Spehar et al. | 366/339 |
| 4,874,368 A | | 10/1989 | Miller et al. | 604/82 |
| 4,978,336 A | | 12/1990 | Capozzi et al. | 604/82 |
| 4,979,942 A | | 12/1990 | Wolf et al. | 604/83 |
| 5,049,135 A | * | 9/1991 | Davis | 604/181 |
| 5,104,375 A | | 4/1992 | Wolf et al. | 604/56 |
| 5,116,315 A | | 5/1992 | Capozzi et al. | 604/82 |
| 5,185,001 A | | 2/1993 | Galanakis | 604/5 |
| 5,290,259 A | | 3/1994 | Fischer | 604/218 |
| 5,322,510 A | | 6/1994 | Lindner et al. | 604/82 |
| 5,368,563 A | | 11/1994 | Lonneman et al. | 604/82 |

(Continued)

FOREIGN PATENT DOCUMENTS

FR    2 722 104    1/1996

(Continued)

OTHER PUBLICATIONS

International Search Report for Application No. PCT/US03/18591 dated Sep. 30, 2003.

*Primary Examiner* — Nicholas Lucchesi
*Assistant Examiner* — Aarti B Berdichevsky
(74) *Attorney, Agent, or Firm* — Mintz, Levin, Cohn, Ferris, Glovsky & Popeo, P.C.

(57) ABSTRACT

Dispensing assemblies, methods, and kits of parts for dispensing two separate fluids to an treatment site, including entraining non-atomized flow of a first fluid in an atomized flow of a second fluid, delivering a first fluid upstream from a second fluid, delivering a first fluid and a second fluid with re-shapeable malleable tubes, delivering first and second fluids with releasable connectors maintained by a handle assembly, and kits of parts with angularly offset pockets.

2 Claims, 9 Drawing Sheets

U.S. PATENT DOCUMENTS

| | | | | |
|---|---|---|---|---|
| 5,376,079 | A | 12/1994 | Holm et al. | 604/191 |
| 5,445,614 | A | 8/1995 | Haber et al. | 604/89 |
| 5,464,396 | A | 11/1995 | Barta et al. | 604/191 |
| 5,474,540 | A | 12/1995 | Miller et al. | 604/191 |
| 5,520,658 | A | 5/1996 | Holm | 604/191 |
| 5,542,934 | A | 8/1996 | Silver | 604/191 |
| 5,582,596 | A | 12/1996 | Fukunaga et al. | 604/191 |
| 5,584,815 | A | 12/1996 | Pawelka et al. | 604/191 |
| 5,605,255 | A | 2/1997 | Reidel et al. | 222/137 |
| 5,643,206 | A | 7/1997 | Fischer | 604/82 |
| 5,665,067 | A | 9/1997 | Linder et al. | 604/82 |
| 5,725,499 | A | 3/1998 | Silverstein et al. | 604/82 |
| 5,759,171 | A * | 6/1998 | Coelho et al. | 604/82 |
| 5,814,022 | A | 9/1998 | Antanavich et al. | 604/191 |
| 5,851,169 | A | 12/1998 | Meresz et al. | 494/12 |
| 5,887,755 | A | 3/1999 | Hood, III | 222/135 |
| 5,935,437 | A * | 8/1999 | Whitmore | 210/321.6 |
| 5,975,367 | A | 11/1999 | Coelho et al. | 222/137 |
| 5,989,215 | A | 11/1999 | Delmotte et al. | 604/82 |
| 6,001,259 | A | 12/1999 | Whitmore | 210/651 |
| 6,059,749 | A * | 5/2000 | Marx | 604/82 |
| 6,113,571 | A | 9/2000 | Zinger et al. | 604/82 |
| 6,132,396 | A | 10/2000 | Antanavich et al. | 604/82 |
| 6,234,994 | B1 | 5/2001 | Zinger | 604/82 |
| 6,394,982 | B1 | 5/2002 | Ehrenfels | 604/191 |
| 6,444,228 | B1 | 9/2002 | Baugh et al. | 424/530 |
| 6,454,739 | B1 | 9/2002 | Chang | 604/82 |
| 6,458,147 | B1 * | 10/2002 | Cruise et al. | 606/214 |
| 6,475,175 | B1 | 11/2002 | Rivera et al. | 604/6.02 |
| 6,589,153 | B2 | 7/2003 | Dolecek et al. | 494/18 |
| 6,596,180 | B2 | 7/2003 | Baugh et al. | 210/782 |
| 6,605,066 | B1 * | 8/2003 | Gravagna et al. | 604/191 |
| 6,610,033 | B1 * | 8/2003 | Melanson et al. | 604/181 |
| 6,612,975 | B2 | 9/2003 | Malcom et al. | 494/84 |
| 6,719,901 | B2 | 4/2004 | Dolecek et al. | 210/380.1 |
| 6,732,887 | B2 * | 5/2004 | Bills | 222/154 |
| 6,793,828 | B2 | 9/2004 | Dolecek et al. | 210/787 |
| 6,852,099 | B2 * | 2/2005 | Redl et al. | 604/289 |
| 6,884,230 | B1 * | 4/2005 | Epstein et al. | 604/82 |
| 6,921,381 | B2 * | 7/2005 | Spero et al. | 604/82 |
| 6,936,033 | B2 * | 8/2005 | McIntosh et al. | 604/191 |
| 6,939,329 | B1 * | 9/2005 | Verkaart | 604/191 |
| 6,942,639 | B2 * | 9/2005 | Baugh et al. | 604/82 |
| 6,972,005 | B2 * | 12/2005 | Boehm et al. | 604/191 |
| 6,994,686 | B2 * | 2/2006 | Cruise et al. | 604/82 |
| 7,081,103 | B2 * | 7/2006 | Epstein et al. | 604/82 |
| 7,322,956 | B2 * | 1/2008 | Fehr et al. | 604/82 |
| 2001/0031948 | A1 * | 10/2001 | Cruise et al. | 604/191 |
| 2002/0004038 | A1 | 1/2002 | Baugh et al. | 424/93.7 |
| 2002/0032463 | A1 * | 3/2002 | Cruise et al. | 606/214 |
| 2002/0138038 | A1 * | 9/2002 | Ljungquist | 604/82 |
| 2003/0187408 | A1 * | 10/2003 | Marx | 604/236 |
| 2003/0232712 | A1 | 12/2003 | Dolecek et al. | 494/37 |
| 2004/0055937 | A1 | 3/2004 | Dolecek | 210/85 |
| 2004/0167617 | A1 * | 8/2004 | Voellmicke et al. | 623/1.23 |
| 2004/0236262 | A1 * | 11/2004 | McIntosh et al. | 604/4.01 |
| 2005/0096588 | A1 * | 5/2005 | Hagmann et al. | 604/82 |
| 2008/0161757 | A1 * | 7/2008 | Nayak et al. | 604/82 |
| 2008/0161772 | A1 * | 7/2008 | Nayak et al. | 604/506 |
| 2008/0167621 | A1 * | 7/2008 | Wagner et al. | 604/191 |
| 2009/0076459 | A1 * | 3/2009 | Goldberg | 604/191 |

FOREIGN PATENT DOCUMENTS

| | | |
|---|---|---|
| WO | WO 95/31137 | 11/1995 |
| WO | WO 00/16698 | 3/2000 |

* cited by examiner

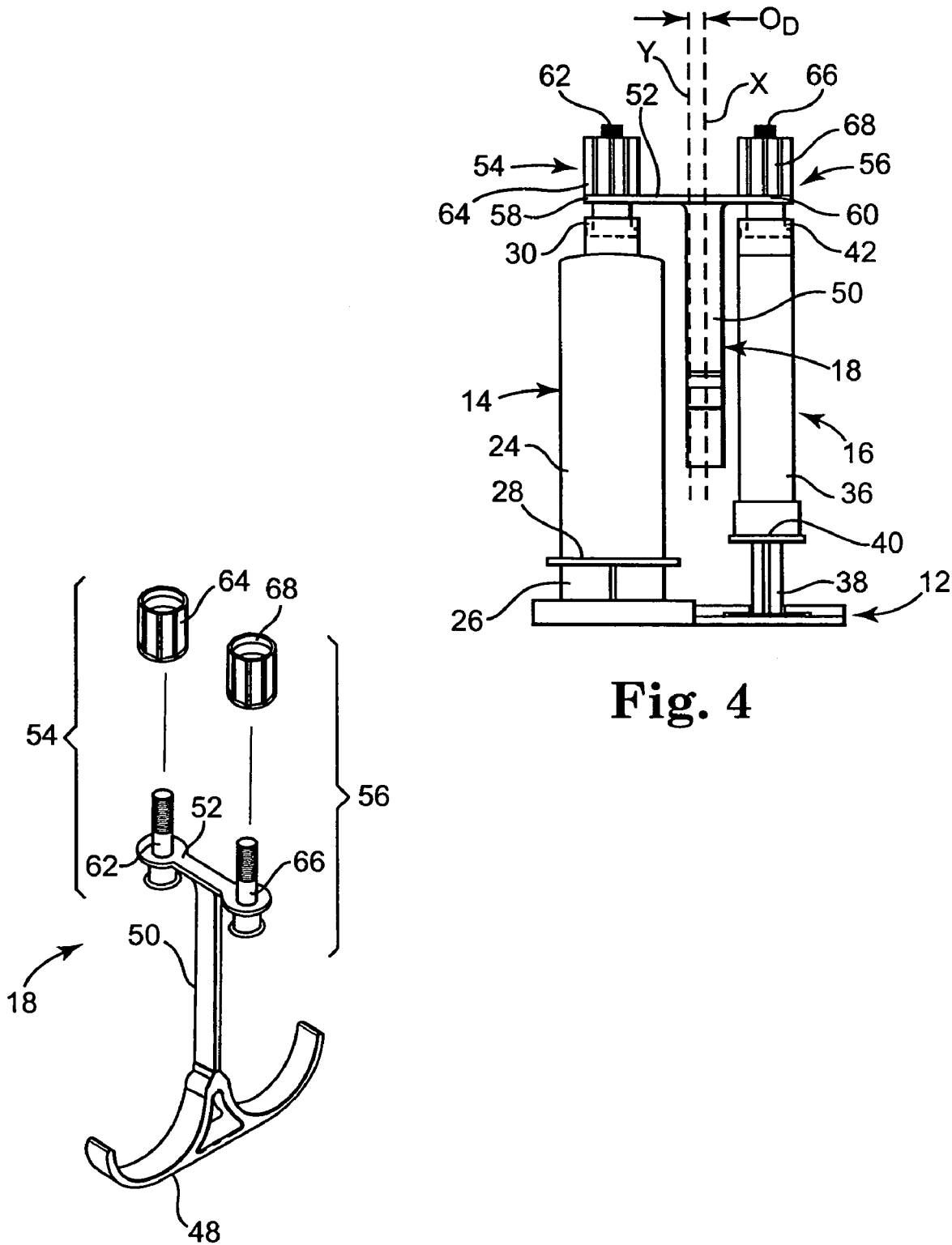

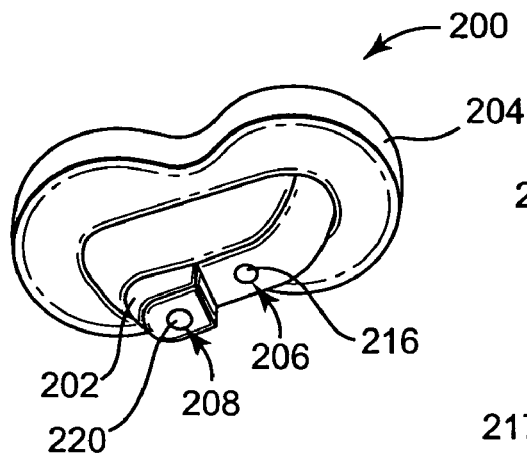
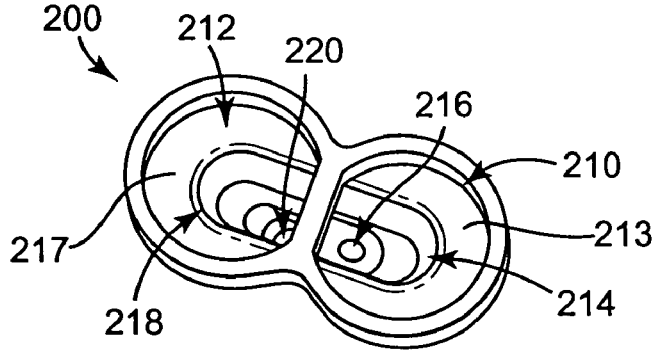
Fig. 12
Fig. 13
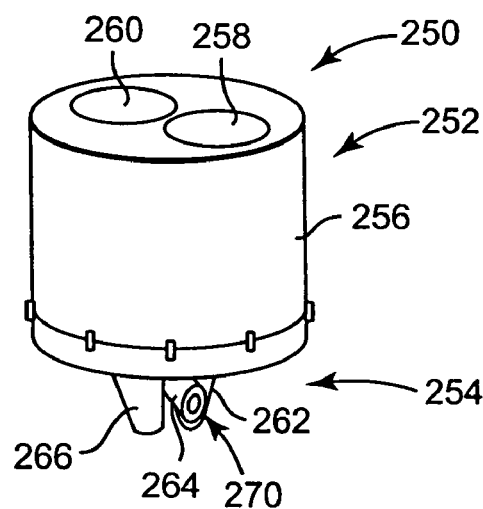
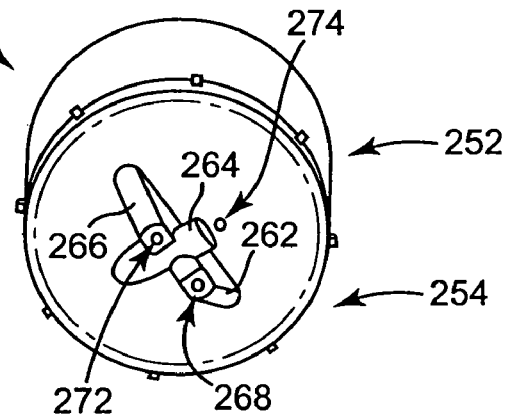
Fig. 14
Fig. 15
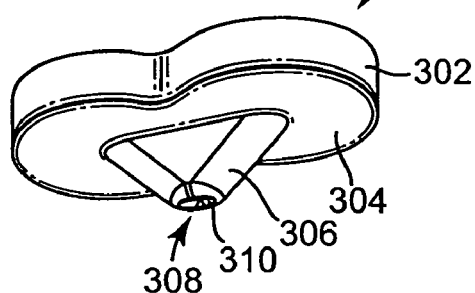
Fig. 16

FLUID DISPENSER

CROSS-REFERENCE TO RELATED APPLICATIONS

This application claims priority to and is a divisional of U.S. patent application Ser. No. 11/341,153, filed Jan. 27, 2006, and claims the benefit under §119(e)(1), and incorporates herein by referenced an entirety of, U.S. Provisional Application No. 60/673,701, filed Apr. 21, 2005, and entitled "Tip and Associated Dispenser." The disclosures of the above applications are hereby incorporated by reference in their entireties.

FIELD OF THE INVENTION

The invention is in the field of systems utilized to apply two or more separate fluids, including freely flowing fluids and viscous fluids or combinations thereof, by delivering them substantially simultaneously to a single location. More particularly, the invention's field concerns systems for simultaneously spraying two or more non-homogeneous materials from two or more syringes.

BACKGROUND

There are a variety of procedures that require the mixing of two or more substances before the mixed compound can be used. Often, the materials that are mixed are volatile, short lived, vulnerable, expensive, precious, unique or irreplaceable.

There are circumstances in which it is desirable to dispense liquid or semi-liquid materials in a predetermined ratio. The materials may include reactive, two component adhesives, sealants, coating, or potting compounds, in which one material may comprise a resin compound and the other material a catalyst.

Dispensers for two or more components are disclosed in U.S. Pat. Nos. 3,223,083; 2,112,160; 5,290,259; 4,609,371; 4,631,055; 4,735,616; 4,874,368 4,978,336; 4,979,942; 5,104,375; 5,116,315; 5,185,001; 5,290,259; 5,322,510; 5,368,563; 5,376,079; 5,464,396; 5,474,540; 5,520,658; 5,582,596; 5,584,815; 5,605,255; 5,643,206; 5,665,067; 5,887,755; 5,975,367; 5,989,215; 6,234,994; 6,394,982; 5,368,563; 6,454,739 and 6,132,396.

One dispensing application relates to fibrin. Clotting of blood in vivo takes place by conversion of the soluble plasma protein fibrinogen into fibrin, which spontaneously polymerizes into an insoluble gel matrix that can attach to adjacent tissue. The gel matrix stops bleeding and stabilizes structures. Thrombin catalyzed conversion of fibrinogen to fibrin can be reproduced in vitro and has great utility for adhering tissues and achieving hemostasis. Such fibrin sealants and fibrin glues are available commercially and are also made in blood processing laboratories. Preparation and use of fibrinogen-based sealants have been extensively reviewed.

Fibrin sealants and fibrin glues and adhesives based on combining fibrinogen-containing solutions with thrombin-containing solutions are used to reduce bleeding and restore hemostasis during surgical procedures. They have been known and in use for many years during which fibrin technology has evolved significantly. For example, fibrin clots can be made using different concentrations of fibrinogen in conjunction with the thrombin solution. Subsequent developments in fibrin technology include cryoprecipitate fibrinogen. In some applications, concentrated plasma is used as the fibrinogen component in fibrin sealants.

Similarly, various types of applicators for fibrin glue are known. The chemical and biological properties of liquid resulting from combining fibrinogen and thrombin solutions are sometimes difficult to predict. Because of the rapid polymerization upon intimate interaction of fibrinogen and thrombin, it is desirable to keep these two blood proteins separate until application to the site of use. In practice, the two components are typically dispensed simultaneously from separate syringes and brought together by means of an applicator manifold.

With some known assemblies, a retaining means is used to maintain syringes carrying the dispensing materials. One retaining means includes a generally trough-shaped or sleeve-shaped retaining structure including appropriate troughs or sleeves for receiving the syringe bodies. In addition, the retaining means is provided with finger grips laterally projecting in opposite directions. The retaining structure can include elastically yielding snap-in projections that hold the syringe bodies. To actuate the pistons of the syringe bodies, a grip element is used. In particular, the grip element is connected to the pistons of the syringes for stabilizing and improving the guidance of the piston rods when actuating the syringe device. It has also been proposed to connect a guide rod with the common grip element. In order to improve tracking, the guide rod extends through a guide bore formed in the retaining means.

Methods for making platelet gels from blood or blood components are also well known. Platelet gels, devices suitable for manufacturing gels from blood components, and methods for making such gels are disclosed in U.S. Pat. Nos. 5,851,169; 6,444,228; 6,475,175; 6,589,153; 6,612,975; 6,596,180; 6,719,901; and 6,793,828 and U.S. Pat. App. Pub. Nos. 2004-0055937 and 2003-0232712. The entire contents of each of these patents and applications are incorporated herein by reference.

Dispensers suitable for applying a gel-like substance (e.g. a platelet gel) to a body are disclosed in U.S. Pat. App. Pub. Nos. 2002-0004038 A1 and 2003-0233067 A1.

Improvements in sprayer type applicator tips remain to be realized. For example, sprayer type applicator tips where a volumetric ratio of the two separate fluids to be dispensed is from 3:1 to 10:1 can encounter significant difficulties. In particular, in some spray applicator systems currently available, the larger volume fluid tends to atomize with ease while the lesser volume fluid will only drip or marginally atomize from respective spray nozzles. This problem can become even more significant when it is desired to have the two components mix as they are applied to a treatment site. Where there is a base media (e.g., platelet rich plasma) and an activator (e.g., thrombin) that can mix and create a fluid that can solidify or gel in as little as 2 seconds, prior art commercialized devices can encounter problems with clogging, providing optimal mixing, and achieving a desired spray pattern.

Additionally, some prior art bead type applicators use a form of hypodermic stainless steel needles to create the two lumens. Although this is effective, one significant shortcoming is that these are considered sharps and require great care in the handling, use, and disposal.

Yet another problem encountered in some prior art assemblies resides in retaining structure designs. Such retaining structures are used to hold the syringe barrels in a parallel state, but fail to hold an associated applicator tip attachment. This may lead to undesired leakage or separation of the syringe barrels and the applicator tip due to assembly errors or the forces encountered during use.

SUMMARY

One embodiment of the present invention provides a tip assembly for use in dispensing a first fluid maintained in a first syringe assembly and a second fluid maintained in a second syringe assembly to a treatment site of a patient. The tip assembly includes a connecting element and a tip element. The connecting element defines a first chamber configured to be in fluid communication with a first syringe assembly and a second chamber configured to be in fluid communication with a second syringe assembly. The tip element includes a nozzle and defines a first orifice and a second orifice. The first orifice extends from an origin to a terminal end with the origin in fluid communication with the first chamber. The second orifice extends through the nozzle from an origin to a terminal end with the origin in fluid communication with the second chamber. In terms of the relative position of the two orifices, the terminal end of the second orifice resides in a different plane than the terminal end of the first orifice.

Another embodiment of the present invention provides a method of dispensing two separately maintained fluids to a treatment site of a patient. The method includes providing a fluid delivery system. The fluid delivery system includes a first syringe assembly maintaining a first fluid and a second syringe assembly maintaining a second fluid. The system also includes a tip element. The tip element defines a first orifice and a second orifice. The first orifice extends to a terminal end and is in fluid communication with the first syringe assembly. The second orifice extends to a terminal end and is in fluid communication with the second syringe assembly. The method also includes dispensing a first flow of the first fluid from the terminal end of the first orifice into a second flow of the second fluid from the terminal end of the second orifice, wherein the first and second flows differ in flow type.

Yet another embodiment of the present invention provides a manifold assembly for use in fluid dispensing system for delivering two separately maintained fluids to a treatment site of a patient. The manifold assembly includes a mating fixture, a first tube, and a second tube. The mating fixture is coupleable to a first syringe assembly and a second syringe assembly. The first tube includes a flexible body and is in fluid communication with the mating fixture. The first tube is also fluidly coupleable to a tip assembly having a first orifice and a second orifice. The first and second orifices are for delivering a first fluid and a second fluid, respectively. The second tube also includes a flexible body with the second tube in fluid communication with the mating fixture and fluidly coupleable to the tip assembly.

Still another embodiment of the present invention provides a method of dispensing two separately maintained fluids to a treatment site of a patient. The method includes providing a fluid dispensing system. The system includes a first syringe assembly maintaining a first fluid and a second syringe assembly maintaining a second fluid. The system also includes a tip assembly defining a first orifice and a second orifice and a manifold assembly. The manifold assembly includes a first tube and a second tube. The first tube includes a flexible body and is in fluid communication with the first syringe and fluidly coupleable to the tip assembly. The second tube includes a flexible body and is in fluid communication with the second connector and fluidly coupleable to the tip assembly. In particular, the method includes cutting the first and second tubes to a desired length and fluidly coupling the first tube and the tip assembly, such that the first tube is in fluid communication with the first orifice. The method also includes fluidly coupling the second tube and the tip assembly, such that the second tube is in fluid communication with the second orifice. The first fluid is delivered from the first syringe assembly, through the first tube, to the first orifice and the second fluid is delivered from the second syringe assembly, through the second tube, and to the second orifice.

Another embodiment of the present invention provides a handle assembly for use in fluid delivery system for delivering two separately maintained fluids to a treatment site of a patient. The handle assembly includes a latitudinal member, a first connector, a second connector, and a longitudinal stem. The latitudinal member extends from a first end to a second, opposing end and defines a centerline between the two ends. The first connector is located at the first end of the latitudinal member and is releasably and fluidly coupleable to a first syringe. The second connector is located at the second end of the latitudinal member and is releasably and fluidly coupleable to a second syringe. The longitudinal stem extends from the latitudinal member at an offset to the centerline of the latitudinal member.

Yet another embodiment of the present invention provides a kit of parts associated with a fluid dispensing system for dispensing two separately maintained fluids to a treatment site of a patient. The kit includes a first syringe, a first specimen cup, and a tray. The first syringe is for delivering a first fluid and the first specimen cup maintains the first fluid prior to delivery. The tray defines a bottom support surface for maintaining the tray in a horizontal position. The tray also defines a pocket for maintaining the first specimen cup in a vertically tipped position. In particular, the pocket defines an angular offset to the horizontal position.

BRIEF DESCRIPTION OF THE DRAWINGS

FIG. 3 is a side view of one embodiment handle assembly assembled to embodiment syringe assemblies of the system of FIG. 1;

FIG. 4 is an exploded, perspective view of the handle assembly of FIG. 3;

FIG. 12 is a perspective view of another embodiment tip element in accordance with the present invention;

FIG. 13 is another perspective view of the tip element of FIG. 12;

FIG. 14 is a perspective view of another embodiment tip assembly in accordance with the present invention;

FIG. 15 is another perspective view of the tip assembly of FIG. 14;

FIG. 16 is a perspective view of another embodiment tip element in accordance with the present invention;

DETAILED DESCRIPTION OF THE INVENTION

Figure 1:
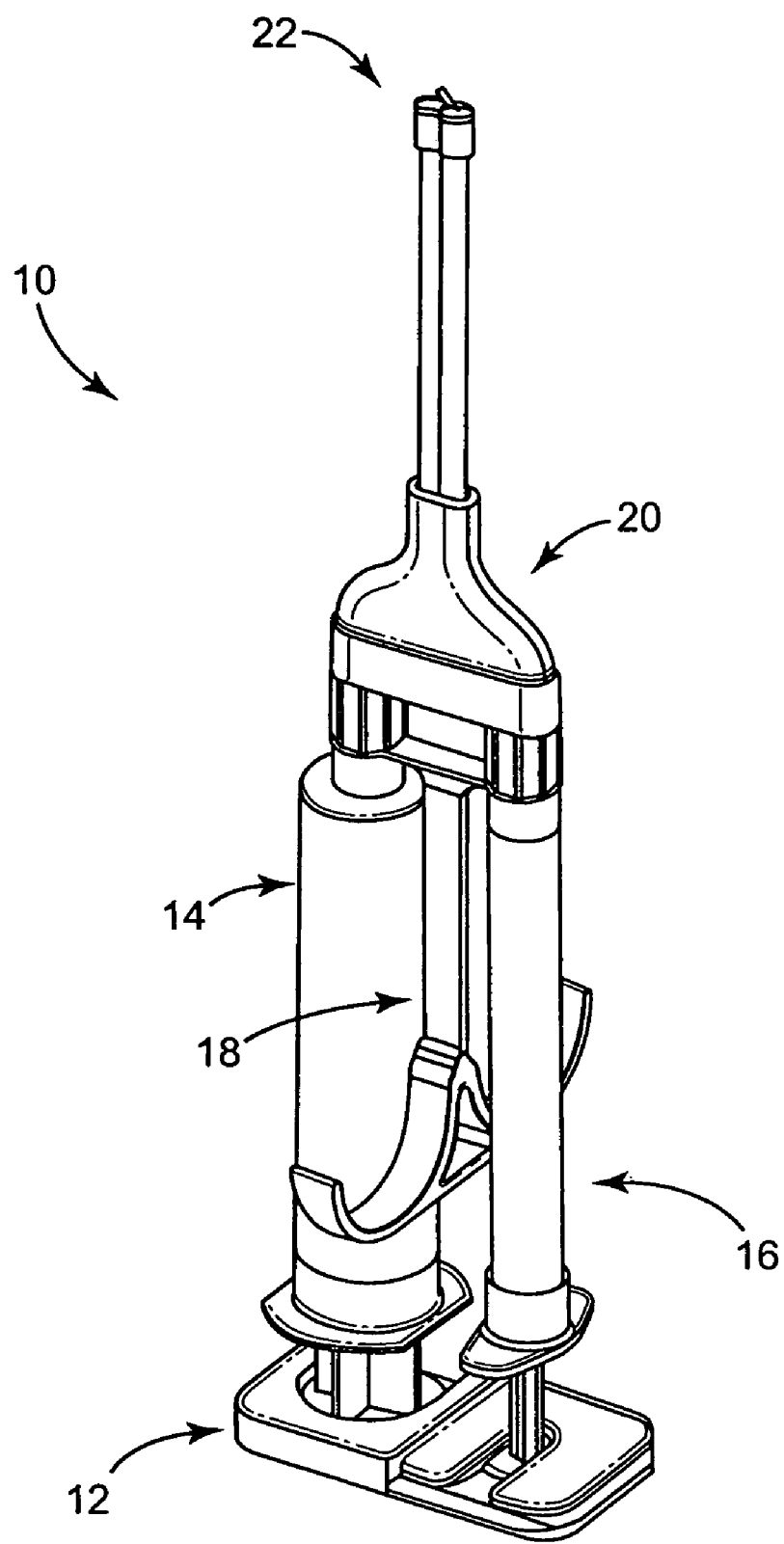
FIG. 1 is a perspective view of one embodiment fluid dispensing system in accordance with principles of the present invention.

One embodiment of a fluid dispensing system 10 is shown in FIG. 1. The fluid dispensing system 10 includes a clip assembly 12, a first syringe assembly 14, a second syringe assembly 16, a handle assembly 18, a manifold assembly 20, and a tip assembly 22. In general terms, the clip assembly 12 and handle assembly 18 can be grasped and manipulated to simultaneously actuate the first and the second syringe assemblies 14, 16 to deliver separately maintained fluids (not shown) from the syringe assemblies 14, 16 through the manifold assembly 20, and to the tip assembly 22. As will be understood in greater with reference to the text that follows, embodiments of the system 10 can provide advantages in mixing the separately maintained fluids upon dispensing them. For example, the system 10 can be used to dispense reactive therapeutic agents, medicaments, tissue sealants, and/or tissue glues, for example, platelet rich plasma and thrombin.

Figure 2:
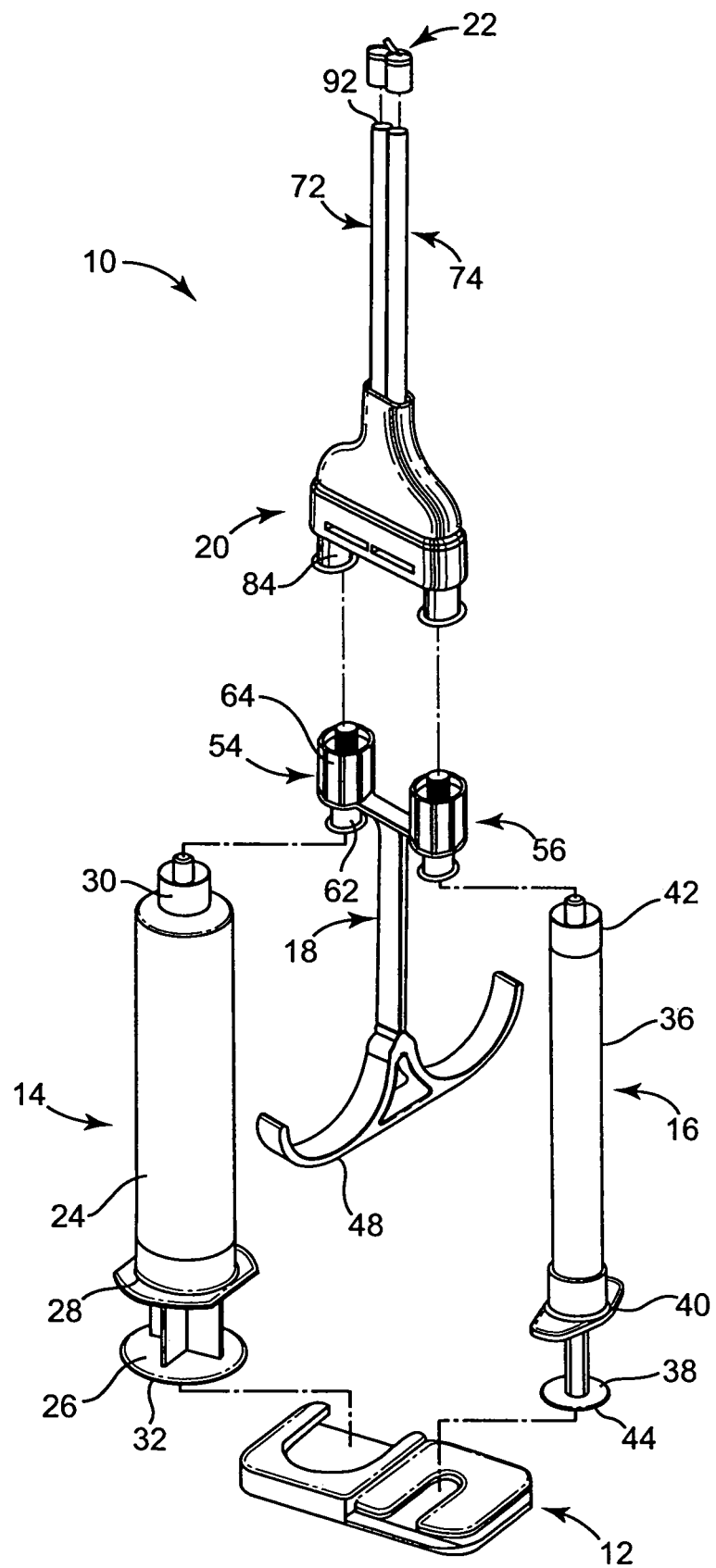
FIG. 2 is an exploded, perspective view of the system of FIG. 1.

With reference to FIG. 2, in one embodiment the clip assembly 12 is configured to allow a user (not shown) to actuate the first syringe assembly 14 and the second syringe assembly 16 simultaneously. The first syringe assembly 14 and the second syringe assembly 16 can be of a type known in the art, including those used in various types of medical applications. The first syringe assembly 14 includes a syringe body 24 and a plunger 26. The syringe body 24 defines a proximal end 28, a distal end 30, and an internal lumen (not shown) having a diameter and configured to maintain a volume of fluid. The plunger 26 is coaxially received in the internal lumen and defines a proximal end 32 and a distal end (not shown).

The second syringe assembly 16 includes a syringe body 36 and a plunger 38. The syringe body 36 defines a proximal end 40, a distal end 42, and an internal lumen (not shown) having a diameter and configured to maintain a volume of fluid. The plunger 38 is coaxially received in the internal lumen and defines a proximal end 44 and a distal end (not shown).

The first syringe assembly 14 maintains a volume of a first fluid (not shown), such as a base fluid, e.g., platelet rich plasma (not shown), while the second syringe assembly 16 separately maintains a volume of a second fluid (not shown), such as an activator fluid, e.g., thrombin. In one embodiment, a portion of the syringe body 24 is color-coded and characterized by a color, for example red, while a portion of the syringe body 36 is characterized by a color, for example white. The colors of the syringe bodies 24, 36 can generally correspond to a color of the first and second fluids, respectively. The plungers 26, 38 can also be characterized by colors such as those described. The first syringe assembly 14 is configured to maintain a larger volume of fluid than the second syringe assembly 16. For example, the syringe body 24 can define a greater diameter than the syringe body 36. The first syringe assembly 14 and the second syringe assembly 16 maintain volumes of the first and second fluids, respectively to define a relative volumetric ratio. In one embodiment, the volumetric ratio of the first and second syringe assemblies 14, 16, is 1:1; in another, the volumetric ratio is 3:1; in another, the volumetric ratio is 5:1; in another, the volumetric ratio is 10:1; and in yet another, the volumetric ratio is 11:1. However, it should be understood that other ratios can be equally acceptable, for example ratios in a range of 1:1 to 10:1, greater than 11:1, or less than 1:1.

In one embodiment, the system 10 is configured to deliver a higher volumetric flow rate of the first fluid (not shown) than a volumetric flow rate of the second fluid (not shown). For example, where the internal lumen (not shown) of the syringe body 24 is of a greater diameter than the internal lumen (not shown) of the syringe body 36, simultaneous actuation of the plungers 26 and 38, for example via the clip assembly 12, results in a higher volumetric flow rate of the first fluid from the syringe assembly 14 than the second fluid from the second syringe assembly 18.

With reference to FIG. 3, the handle assembly 18 can be described in greater detail. The handle assembly 18 includes a grasping portion 48, a longitudinal stem 50, latitudinal member 52, a first connector 54, and a second connector 56. The grasping portion 48 extends from the longitudinal stem 50 and can help allow a user to simultaneously impart a force on the grasping portion 48, for example with a middle finger (not shown) and a ring finger (not shown), and a complementary force on the clip assembly 12 (FIG. 2), for example with a thumb (not shown).

With reference to FIG. 4, the longitudinal stem 50 defines a longitudinal axis X and, in turn, extends proximally from the latitudinal member 52. The latitudinal member 52 extends between a first end 58 and an opposing second end 60 and defines a center between the first and second ends 58, 60 along a centerline Y. As shown the first and second connectors 54, 56 are opposingly located relative to the center at the first and second ends 58, 60, respectively of the latitudinal member 52. In one embodiment, the longitudinal stem 50 extends at an offset from the latitudinal member 52. For example, the longitudinal axis X can define an offset distance $O_D$ from the centerline Y. From this, it should be understood that the longitudinal stem 50 can also reside at an offset from the center between the first and second connectors 54, 56.

With reference between FIGS. 3 and 4, the first and second connectors 54, 56 are configured to receive the distal ends 30, 42 of the first and second syringe assembly syringe bodies 24, 36, respectively. For example, in one embodiment, the first and second connectors 54, 56 are luer fittings. As such, the first connector 54 can include a tubular portion 62 and a male fitting 64. The tubular portion 62 is formed through the first end 58 of the latitudinal member 52 and defines a fluid passageway for conveying fluid (not shown) from the first syringe assembly 14. In one embodiment, the first connector 54 is color-coded. For example, the male fitting 64 can be characterized by a color such as red.

In turn, the second connector 56 can also include a tubular portion 66 and a male fitting 68. The tubular portion 66 is formed through the second end 60 of the latitudinal member 52 and defines a fluid passageway for conveying the second fluid (not shown). In one embodiment, the second connector 56 is color-coded. For example, the male fitting 68 can be characterized by a color such as white.

As shown in FIG. 4, the longitudinal stem 50 is situated at the offset distance $O_D$ such that a larger sized syringe body (e.g., syringe body 24) can only fit on a predetermined side of the handle assembly 18. For example, the offset distance $O_D$ can be selected to restrict which syringe body 24, 36 can be coupled to which of the first and second connectors 54, 56. In one embodiment, the longitudinal stem 50 is positioned relative to the first and second connectors 54, 56 such that the first syringe assembly 14 cannot be coupled to the second connector 56. As will be understood in greater detail below, predetermining to which side the syringe assemblies 14, 16 are properly connectible can ensure that the first fluid (not shown) and the second fluid (not shown) are delivered to an appropriate part of the tip assembly 22.

Figure 5:
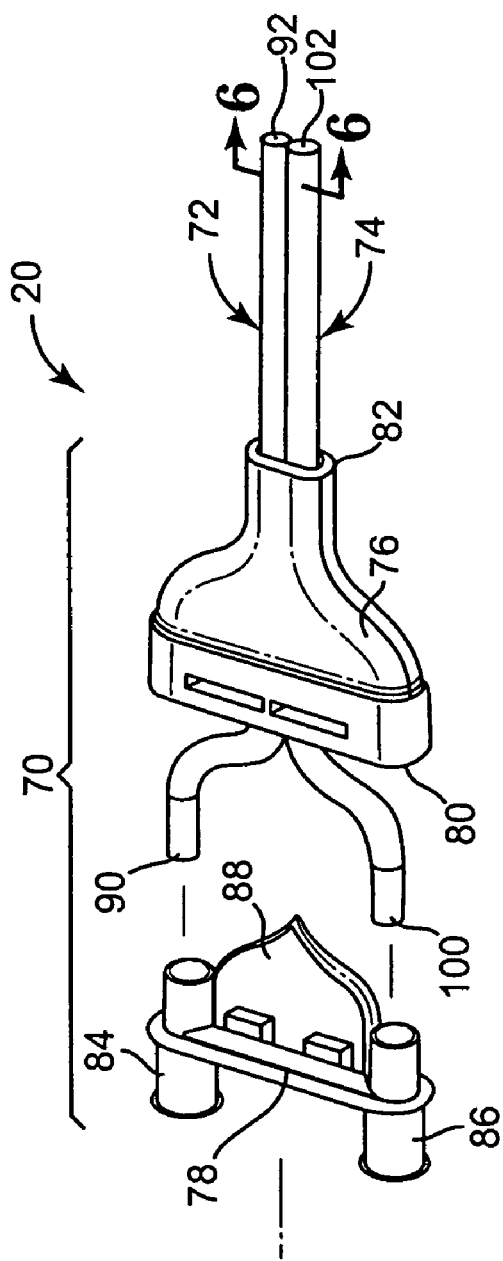
FIG. 5 is an exploded, perspective view of one embodiment manifold assembly of the system of FIG. 1.

With reference to FIG. 5, the manifold assembly 20 includes a jacket 70, a first tube 72, and a second tube 74. In general terms, the manifold assembly 30 is configured to facilitate fluid communication between contents of the first and second syringe assemblies 14, 16 (FIG. 2) and the tip assembly 22 (FIG. 2).

The jacket 70 includes a hollow sleeve 76 and a mating fixture 78. It should be noted that in FIG. 5, the sleeve 76 is shown slid distally down the first and second tubes 72, 74 relative to the assembled configuration of the manifold assembly 20 shown in FIG. 2. With that in mind, the hollow sleeve 76 defines a proximal end 80 and a distal end 82. The mating fixture 78 is configured to be coupled to the proximal end 80 of the hollow sleeve 76, for example via a snap fit. The mating fixture 78 includes a first fitting extension 84, a second fitting extension 86, and a tube guide 88. The first and second fitting extensions 84, 86 each define an inner lumen (not shown) configured to be fluidly coupled to the first and second tubes 72, 74, respectively, and to mate with or otherwise be fluidly coupleable to the first and second connectors 54, 56 (FIG. 3) of the handle assembly 18 (FIG. 3).

The tube guide 88 is configured to assist in maintaining the first and second tubes 72, 74 within the hollow sleeve 76. As shown, the tube guide 88 can be generally v-shaped or otherwise configured to secure and guide the tubes 72, 74 from a laterally spaced configuration at the proximal end 80 of the hollow sleeve 76 to an adjacent position at the distal end 82 of the hollow sleeve 76.

Figure 6:
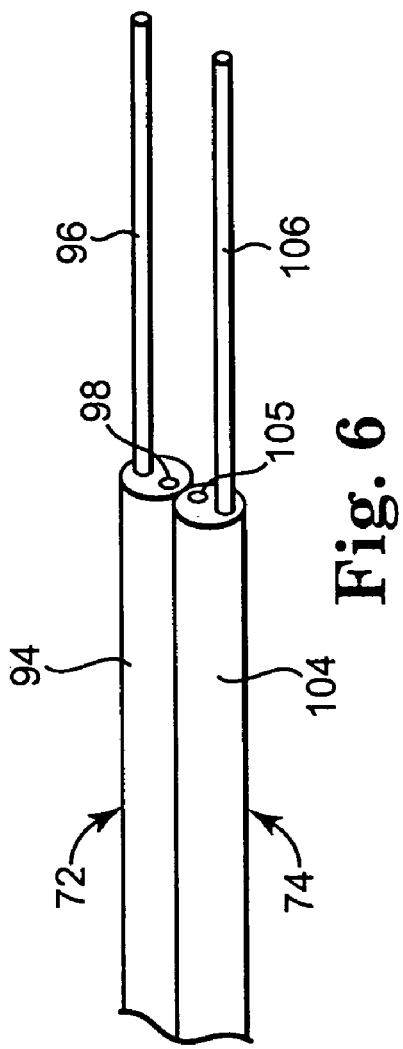
FIG. 6 is a cut-away, perspective view of embodiment first and second tubes of the manifold assembly of FIG. 5 cut-away along line 6-6 of FIG. 5.

With additional reference to the partially cut-away view of FIG. 6, the first and second tubes 72, 74 can be described in greater detail. In general terms, the first and second tubes 72, 74 can be distinctly formed, or can be formed jointly, for example with a thin piece of material connecting the first and second tubes together along a portion or entire length of the first and second tubes 72, 74. The first tube 72 can be flexible, rigid, or semi-rigid. In one embodiment, the first tube 72 is semi-rigid, defines a proximal end 90 and a distal end 92 and includes a flexible body 94 and a bendable member 96 that is malleable. The flexible body 94 defines a first inner lumen 98 configured to receive and convey the first fluid (not shown). In one embodiment, the flexible body 94 defines a second inner lumen (not shown) configured to coaxially receive the bendable member 96. In one embodiment, the flexible body 94 can be formed over the bendable member 96 such that the second inner lumen is defined upon formation of the flexible body 94 over, or about, the bendable member 96. In another embodiment, the bendable member 96 can be inserted into the second inner lumen.

The flexible body 94 can be constructed from a flexible, sterilizable material such as PVC or polyurethane. An outer diameter of the flexible body 94 can be approximately 0.125 inches, although other dimensions are equally acceptable. The first inner lumen 98 and/or the second inner lumen (not shown) can define diameters of approximately 0.035 inches, although other dimensions are equally acceptable. The flexible body 94 can define a variety of lengths for adaptation to specific application needs. As will be described below, in one embodiment, the first tube 72, including the flexible body 94 and bendable member 96, can be cut (using surgical scissors, for example) to a desired length.

In one embodiment, the bendable member 96 is an elongate and malleable. For example, the bendable member 96 can be a malleable, re-bendable wire, such as a stainless steel wire. In this manner, the flexible body 94 can be provided with a malleable "backbone" to allow selective shaping, or bending of the first tube 72 such that the first tube 72 is semi-rigid. Due to the malleable nature of the bendable member 96, the flexible body 94 can be selectively repositioned in different orientations which are independently retained by first tube 72 after repositioning. In this manner, the first tube 72 can be manually transitioned from a first non-bent state, to semi-rigidly define a first bend (not shown), a second bend (not shown), a third bend (not shown) and so forth. In one embodiment, the first tube 72 can be shaped to facilitate dispensing the first and second fluids (not shown) to a desired location.

In one embodiment, the first tube 72 is color-coded and characterized by a color, such as red. For example, the flexible body 94 of the second tube 72 can be red. Additionally, it should be noted that in some embodiments, a reduced diameter first tube 72 is desired. For example, the flexible body 94 can define a single inner lumen (not shown) and be characterized by the absence of the bendable member 96. In this manner, in one embodiment the first tube 72 can be completely flexible. In terms of use, there are several applications where a longer first tube 72 of a smaller diameter and increased flexibility are preferred (e.g., for vascular insertion or for reaching remote treatment sites).

In one embodiment, the second tube 74 is substantially similar to the first tube 72. For example, the second tube 74 can also define a proximal end 100 (FIG. 5) and a distal end 102 (FIG. 5) and include a flexible body 104 defining an inner lumen 105 and a bendable member 106. In this manner, the flexible body 104 can similarly be provided a malleable "backbone" via the bendable member 106 to allow selective shaping, or bending of the second tube 74. However, in another embodiment, the bendable member 96 of the first tube 72 can alone be used, without use of the bendable member 106, to allow selective shaping of both the first and the second tubes 72, 74. Regardless, in one embodiment, the second tube 74 is color-coded and characterized by a color, such as white. For example, the flexible body 104 of the second tube 74 can be white.

With reference to FIG. 5, the manifold assembly 20 can be assembled as shown in FIG. 2 by fluidly coupling the proximal end 90 of the first tube 72 to the first fitting extension 84 of the mating fixture 78, and the second tube 74 to the second fitting extension 86. The first and second tubes 72, 74 can be directed out of the distal end 82 of the hollow sleeve 76. The mating fixture 78 can then be secured to the proximal end 80 of the hollow sleeve 76, for example via a snap fit.

Figure 7:
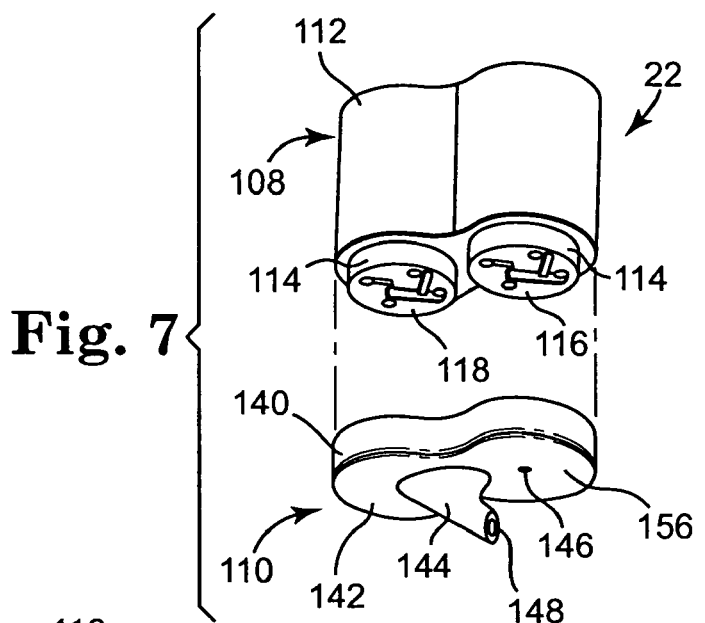
FIG. 7 is an exploded, perspective view of one embodiment tip assembly of the system of FIG. 1.

With reference to FIG. 7, the tip assembly 22 includes a connecting element 108 and a tip element 110. In general terms, the connecting element 108 is coupled to the tip element 110 such that the two are in fluid communication. In one embodiment, the connecting element 108 includes a sidewall 112, and an endwall 114 forming a first distal projection 116 and a second distal projection 118.

Figure 9:
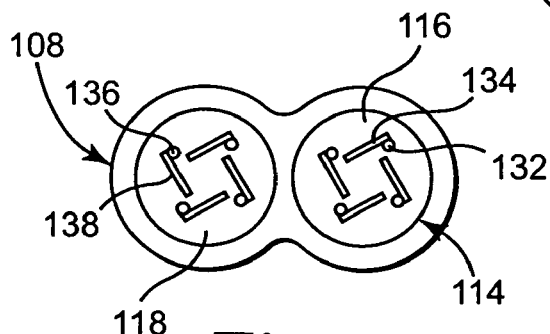
FIG. 9 is a bottom view of the connecting element of FIG. 8.
Figure 8:
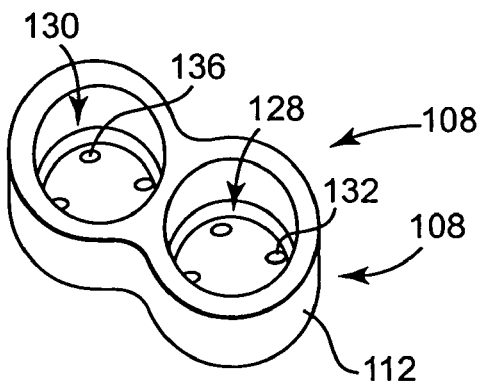
FIG. 8 is a perspective view of one embodiment connecting element of the tip assembly of FIG. 7.

With reference between FIGS. 8 and 9, the sidewall 112 of the connecting element 108 defines a first chamber 128 and a second chamber 130. The first chamber 128 is open opposite the endwall 114. The first distal projection 116 has a hole 132 extending through the endwall 114 to the first chamber 128. A channel 134 is formed in the endwall 114, and in particular the first distal projection 116, but not through an entirety thereof. The channel 134 extends tangentially from the hole 132 and defines a cross-sectional area. The channel 134 is approximately 0.003 to approximately 0.006 inches in width in one embodiment, although other dimensions can be equally acceptable. In this manner, the channel 134 is in fluid communication with the first chamber 128 via the hole 132. As shown, the hole 132 can be a first one of a plurality of holes and the channel 134 can be a first one of a plurality of channels extending tangentially from a corresponding one of the plurality of holes.

The second chamber 130 can be similarly formed to the first chamber 128 with the second chamber 130 open opposite the endwall 114. In one embodiment, the second distal projection 118 has a hole 136 extending through the endwall 114 to the second chamber 130. A channel 138 can also be formed in the endwall 114, and in particular the distal projection 118, but not through an entirety thereof. The channel 138 extends a length tangentially from the hole 136 and defines a cross-sectional area. The channel 138 is approximately 0.003 to approximately 0.006 inches in width in one embodiment, although other dimensions can be equally acceptable. Regardless, the channel 138 is in fluid communication with the second chamber 130 via the hole 136. Additionally, and as shown, the hole 136 can be a first one of a plurality of holes and the channel 138 can be a first one of a plurality of channels extending tangentially from a corresponding one of the plurality of holes.

With additional reference to FIG. 7, the tip element 110 includes a sidewall 140, an endwall 142, and a nozzle 144 extending from the endwall 142. In general terms, the tip element 110 can also have a first orifice 146 and a second orifice 148.

Figure 10:
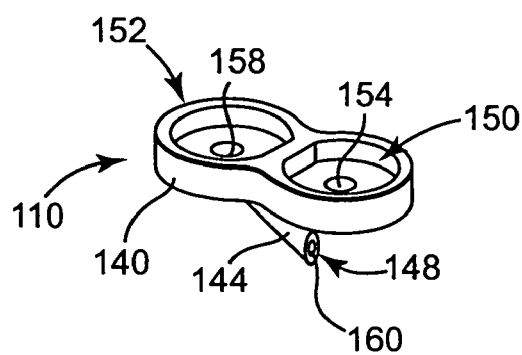
FIG. 10 is a perspective view of one embodiment tip element of the tip assembly of FIG. 7.

With reference between FIGS. 7 and 10, in one embodiment, the sidewall 122 can define a first receptacle 150 open opposite the endwall 142 and a second receptacle 152 open opposite the endwall 142. In one embodiment, the first receptacle 150 and the first distal projection 116 of the connecting element 108 can have complementary shapes, such that the first distal projection 116 is received within the first receptacle 150 of the tip element 110. In turn, the second receptacle 152 and the second distal projection 118 can also be complementary in nature, such that the second distal projection 118 is receivable within the second receptacle 152.

Figure 11:
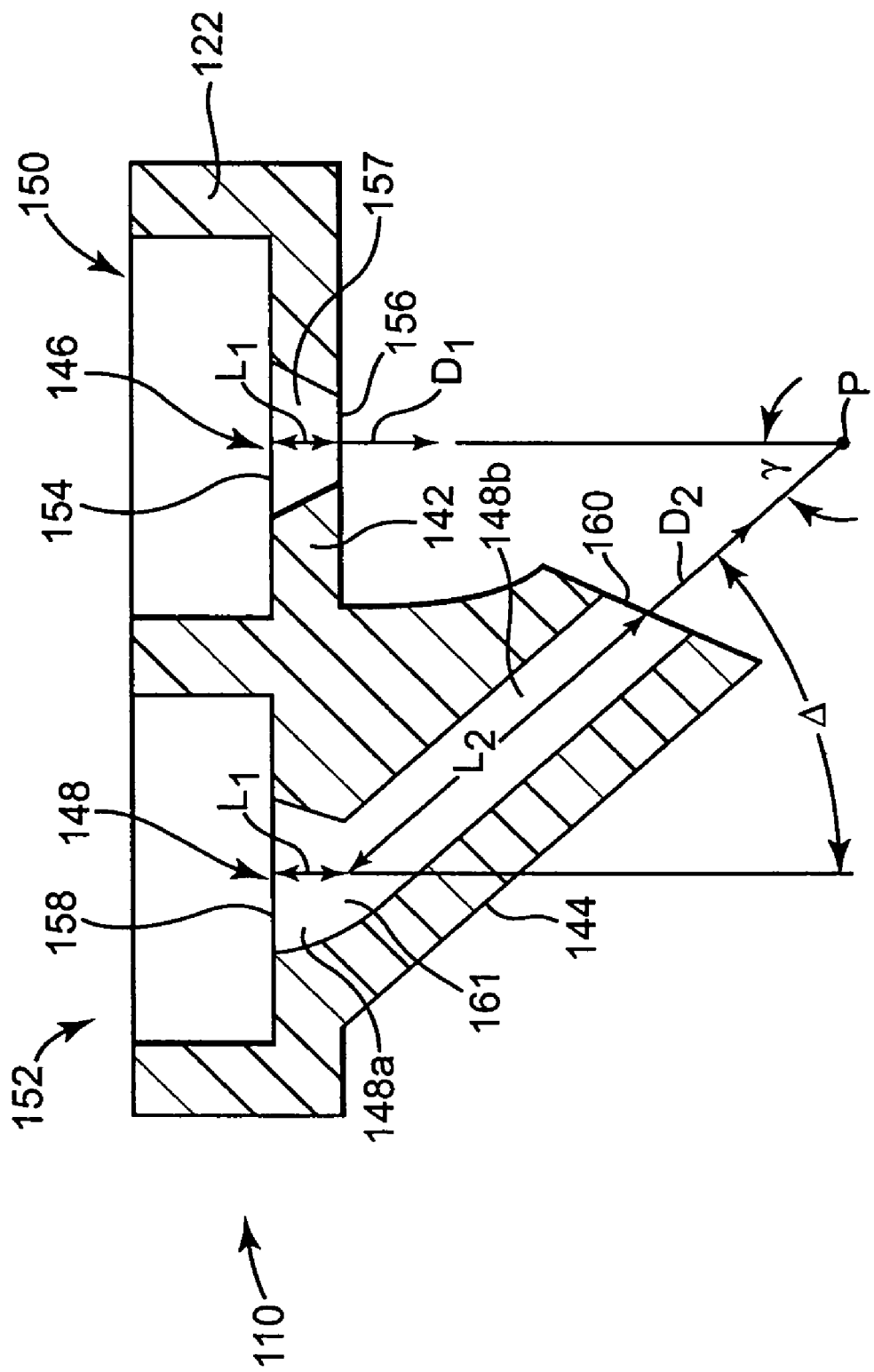
FIG. 11 is a cross-sectional view of the tip element of FIG. 10.

With reference to FIG. 11, the first orifice 146 extends for a length $L_1$ through the endwall 142 from an origin 154 open to the first receptacle 150 to a terminal end 156. The first orifice 146 extends to the terminal end 156 to define a first flow direction $D_1$ and defines a volume 157. The first orifice 146 can taper from the origin 154 to the terminal end 156. For example, a diameter of the first orifice 146 at the origin 154 can be greater than a diameter of the first orifice 146 at the terminal end 156 to define a taper. Additional tapers are also contemplated in some embodiments. For example, in one embodiment, the first orifice 146 includes a first taper from a first, larger diameter to a second smaller diameter, and a second taper from the smaller diameter to a third, larger diameter (not shown).

In one embodiment, the terminal end 156 of the first orifice 146 is approximately 0.006 inches to approximately 0.020 inches in diameter, although other dimensions can be equally acceptable depending on the volume and type of fluid being atomized, for example. Additionally, the length $L_1$ can be approximately 0.05 inches, although other dimensions can be equally acceptable.

The second orifice 148 includes a first portion 148a formed in the endwall 142 and a second portion 148b formed in the nozzle 144. The first portion 148a defines an origin 158 of the second orifice 148 and can be described similarly to the first orifice 146. In particular, the first portion 148a extends the length $L_1$ through the endwall 142. The first portion 148a defines a taper from a first diameter at the origin 158 through the endwall 142 to a second, smaller diameter.

As shown, the second portion 148b is formed through the nozzle 144. The nozzle 144 extends distally from the endwall 142 at or through an angle Δ. In one embodiment, the angle Δ is approximately 45 degrees, although other dimensions can be equally acceptable. As formed, the second portion 148b extends for a length $L_2$ to define a terminal end 160 of the second orifice 148. In particular, the second portion 148b extends to the terminal end 160 to define a second flow direction $D_2$. In one embodiment, the second orifice 148, including the first and second portions 148a, 148b, defines a volume 161. It should be understood that the lengths $L_1$, $L_2$ as well as the diameter(s) of the second orifice 148 can be selected to adjust the volume 161 of the second orifice 148. In one embodiment, the volume 161 of the second orifice 148 is greater than the volume 157 of the first orifice 146.

As shown in FIG. 11, angular extension of nozzle 144 results in the terminal end 160 of the second orifice 148 being located or offset distally to the terminal end 156 of the first orifice 146. In different terms, the first and second orifices 146, 148, and in particular the terminal ends 156, 160, each reside in a different plane from the other, such that the two orifices 146, 148 terminate in different planes. In this particular, the terminal end 160 can be located offset and down stream from the terminal end 156. Furthermore, the directions $D_1$, $D_2$ can be angularly offset at an angle γ, for example approximately 45 degrees. In another embodiment, the angle γ is approximately 90 degrees such that the directions $D_1$, $D_2$ are substantially perpendicular. As shown, the two directions $D_1$, $D_2$ can intersect at a point P distal the terminal end 156 of the first orifice 146 and spaced laterally from the terminal end 160 of the second orifice 148. For example, the point P can be laterally spaced a distance of approximately 0.020 inches from the terminal end 160, although other dimensions can be equally acceptable. As will be described in the text that follows, the angle Δ and length $L_2$ of the nozzle 144 can be selected such that the second fluid (not shown) is delivered from the terminal end 160 of the second orifice 148 into a flow of the first fluid (not shown) from the terminal end 156 of the first orifice 146.

With reference between FIGS. 7 and 10, the tip assembly 22 is assembled by inserting the first distal projection 116 of the connecting element 108 into the first receptacle 150 of the tip element 110 and the second distal projection 118 into the second receptacle 152. The connecting element 108 and tip element 110 can be secured together via an interference-type fit, glues, welding, magnets, etc. The origin 154 of the first orifice 146 is tangentially related to the channel 134 when the connecting element 108 and the tip element 110 are assembled. In this manner, the first orifice 146 of the tip element 110 is in fluid communication with the first chamber 128 of the connecting element 108. It should be understood that, as shown, the channel 134 and associated plurality of channels of the distal projection 116 are tangentially related to the origin 154 of the first orifice 146. In this manner, the origin 154 of the first orifice 146 is centrally located relative to the plurality of channels such that each channel can deliver a tangential flow of fluid to the first origin 154. The channel 138, as well as the plurality of channels, of the distal projection 118 can be similarly in fluid communication with the origin 158 of the second orifice 148. As will be understood in greater detail with reference to the following text, the tangential relationships described above facilitate rotational acceleration of the first and the second fluids (not shown) as they move into the origins 154, 158 of the first and second orifices 146, 148 respectively.

With reference to FIG. 2, an exemplary assembly of the fluid dispensing system 10 as shown in FIG. 1 can be described. The clip assembly 12 is fastened to the proximal ends 32, 44 of the plungers 26, 38 of the first and second syringe assemblies 14, 16, respectively. The distal end 30 of the syringe body 24 of the first syringe assembly 12 is fluidly coupled to the first connector 54 of the handle assembly 18. In particular, the distal end 30 is fluidly coupled to the tubular portion 62 of the first connector 54 such that the first syringe assembly 14 is in fluid communication with the tubular portion 62 of handle assembly 18. The distal end 30 of the syringe body 24 is screwed over the tubular portion 62. The second syringe assembly 16 is similarly coupled to the second connector 56 of the handle assembly 18.

In one embodiment, the first and second connectors 54, 56 of the handle assembly 18 are, in turn, fluidly coupled to the manifold assembly 20 such that the handle assembly 18 is in fluid communication with the manifold assembly 20. In particular, the tubular portion 62 of the first connector 54 is inserted into the first fitting extension 84 and the male fitting 64 is screwed over the first fitting extension 84 to form a secure fit. In this manner, the tubular portion 62 is in fluid communication with the fitting extension 84, which, in turn, is in fluid communication with the first tube 72, and in particular the inner lumen 98 (FIG. 6).

In one embodiment, the second connector 56 is similarly fluidly coupled to the manifold assembly 20 such that the handle assembly 18 is in fluid communication with the manifold assembly 20, and in particular the second tube 74. It should be understood that in one embodiment, the connectors 54, 56, such as luer fitting-type connectors, allow for quick disconnect, reconnect, and a structurally secure and fluid conveying fit between the syringe assemblies 14, 16 and the manifold assembly 20 via the handle assembly 18. In this manner, first and second connectors 58, 60 fluidly couple the handle assembly 18 to the manifold assembly 20 independent of other mechanisms. However, while the handle assembly 18 has been described as defining a fluid passageway, it should be understood that other handle assemblies are also implemented in some embodiments of the present invention such that the first and second syringe assemblies 14, 16 are directly fluidly coupled to the manifold assembly 20, for example in a manner similar to that described in U.S. Pat. App. Pub. No. 2003/0233067.

In one embodiment, the distal end 92 of the first tube 72 is inserted into the first chamber 128 (FIG. 8) of the connecting element 108. The first tube 72 can be retained in the first chamber 128 via an interference-type fit, welds, adhesives, etc. In this manner, the inner lumen 98 (FIG. 6) is fluidly coupled with the first chamber 128. The second tube 74 can be similarly assembled to the tip assembly 22 via the second chamber 130 (FIG. 7) and in fluid communication therewith. In one embodiment, the first tube 74 and/or the second tube 76 are trimmed to a desired length prior to assembly with the tip assembly 22. For example, the first and second tube assemblies 74, 76 can be cut using surgical scissors to define new distal ends 92, 102 prior to assembly to the first and second chambers 128, 130, respectively.

A user can be directed as to the proper assembly of the system 10 in some embodiments of the present invention. For example, a user can be keyed to the proper assembly via the color-coding of various elements described above. In one embodiment, portions of the handle assembly 18 and the manifold assembly 20 are characterized by colors, for example red or white to indicate proper assembly of the system 10. It should also be understood that portions of the tip assembly 22 and the first and second syringe assemblies 14, 16 can also be color-coded. In one embodiment, the color-coding of the elements corresponds generally to a color characterizing the first and/or second fluids (not shown), respectively. In other words, a user can be directed to assemble components of system 10 such that a substantially red-colored fluid is dispensed with portions of the system 10 that are colored red. Furthermore, and as described above, the handle assembly 18 can be configured to ensure that a desired one of the syringe assemblies 14, 16 is connected to a pre-selected one of the connectors 54, 56 of the manifold assembly 20. In light of such features, a user can be directed in proper assembly of the system 10 according to from which of the first and the second orifices 146, 148 each of the first and second fluids should be delivered.

From the previous description, it should understood that in one embodiment, assembly of the system 10 results in the first and second syringe assemblies 14 being in fluid communication with the tip assembly 22. In particular, in one embodiment the first syringe assembly 14 is in fluid communication with the first orifice 146 (FIG. 7) and the second syringe assembly 16 is in fluid communication with the second orifice 148 (FIG. 7) such that actuation of the plungers 26, 38 dispense the first and second fluids (not shown) from the first and second orifices 146, 148, respectively. In this manner, the first and second fluids can be dispensed from the first and second orifices 146, 148 to a desired treatment site (not shown).

In light of the relationships described above, one method of delivering the first and second fluids (not shown) to a treatment site (not shown) can be described. In one embodiment, a user simultaneously actuates the first and second syringe assemblies 14, 16 by grasping the grasping portion 48 of the handle assembly 18 and pressing on the clip assembly 12 connected to the plungers 26, 38. Referring back to FIGS. 9 and 10, the first fluid flows through the hole 132 to the channel 134 and is delivered tangentially to, and into, the origin 154 of the first orifice 146. This tangential relationship facilitates rotational acceleration of the first fluid. Furthermore, as described above, a plurality of channels can also be implemented to achieve rotational acceleration of the second fluid. From this, it should be understood that rotation of the second fluid can be similarly achieved at the second orifice 148, with subsequent deceleration occurring in some embodiments. However, it should also be understood that the second distal projection 118 need not include the channel 138 such that the second fluid can flow from the second chamber 130, through the hole 136, and directly into the second orifice 148.

In one embodiment, simultaneous actuation of the first and second syringe assemblies 14, 16 (FIG. 2) results in a greater volumetric flow rate of the first fluid (not shown) to the channel 134 of the first distal projection 116 than a volumetric flow rate of the second fluid (not shown) to the channel 138 of the second distal projection 118. This, in turn, can contribute to greater rotational acceleration (as well as a greater volumetric flow rate) of the first fluid as it enters the origin 154 of the first orifice 146 than the second fluid as it enters the origin 158 of the second orifice 148.

In one embodiment, the rotational acceleration of the first fluid (not shown) facilitates atomization of the first fluid upon exiting the terminal end 156 of the first orifice 146. The amount of fluid rotation can affect the particle size and distribution of the first fluid as well as the overall, mixed fluid properties of the first fluid. The ratio of the cross-sectional area of the channel 134 to the fluid volume, or volumetric flow rate, can affect the amount of rotational acceleration achieved. In other words, a larger volume of fluid flowing through a smaller cross-sectional area can equate to a higher rotational acceleration of the fluid through the cross-sectional area. However, a greater overall volumetric flow rate can be achieved with a larger overall, or "summed," cross-sectional area. As such, one embodiment incorporates more than one channel to optimize rotational acceleration and volumetric flow rates and/or reduce flow resistance in the system 10. For additional understanding, rotation methodology for atomization is described in Chemical Engineer's handbooks such as, Chemical Engineers' Handbook (R. H. Perry & C. H. Chilton eds., 5th ed., McGraw-Hill 1973).

In light of the above, it should also be understood that rotational acceleration of the first and second fluids (not shown) at the origins 154, 158 can be varied by modifying the tip assembly 22, such as by at least one of the following: modifying a total number of channels, modifying a cross-sectional area of such channels, and modifying the diameters of the first and second orifices 146, 148 at the origins 154, 158.

In one embodiment, the tip element 110 is configured to deliver an atomized flow from the first orifice 146. For example, at least one of the taper, the diameter at the origin 154, the diameter at the terminal end 156, and the length $L_1$ of the first orifice 146, can be selected to facilitate production of atomized flow from the first orifice 146. However, it should be understood that in some embodiments other features can be added or modified to facilitate production of atomized flow from the first orifice 146.

In one embodiment, the second fluid (not shown) enters the channel 138 and flows toward the terminal end 160 of the second orifice 148 at a slow enough rate such that there is minimal to no rotational acceleration. The lesser volume fluid flow will have some rotation but not enough for fluid atomization. In the absence of rotation and/or sufficient rotational acceleration, the flow of the second fluid beads or coalesces at the terminal end 160 of the second orifice 148.

The second orifice 148 can also be configured to facilitate delivery of a bead or stream of fluid to a point where an atomized flow of the first fluid (not shown) is coming from the first orifice 146. For example, the nozzle 144 can be configured to assist in decelerating fluid rotation to avoid atomized flow of the second fluid from the second orifice 148. In one embodiment, at least one of the taper, the diameter at the origin 158, the diameter at the terminal end 160, the lengths $L_1$, $L_2$ of the second orifice 148, the volume 161 defined by the second orifice 148, and the angle Δ through which the nozzle 144 extends contribute to rotational deceleration of the second fluid. While the features described above can serve to decrease fluid rotation, or decelerate fluid rotation as it is delivered through the second orifice 148, it should be understood that in some embodiments other features and mechanisms for facilitating drip flow can be added or modified.

Regardless, in one embodiment, the user actuates the first and second syringe assemblies 14, 16 to produce at atomized flow type of the first fluid (not shown) from the terminal end 156 of the first orifice 146 and a non-atomized flow type, such as a drip-flow, of the second fluid (not shown) from the terminal end 160 of the second orifice 148. As alluded to above, the nozzle 144 can be configured to deliver the second fluid distal or downstream to the first fluid. In one embodiment, distally offsetting the terminal end 160 to the terminal end 156 can allow an atomized flow (or at least a portion thereof) of the first fluid to be delivered in the direction $D_1$ from the terminal end 156 of the first orifice 146, travel past the terminal end 160 of the second orifice 158, and entrain a non-atomized flow of the second fluid from the terminal end 160 of the second orifice 158. In this manner, the atomized flow of the first fluid "picks up" beads of second fluid resulting in a thorough mixing of the two fluids after exiting the first and second orifices 146, 148, respectively. In one embodiment, the first and second fluids are mixed at a point distal the terminal end 156 of the first orifice 146 but prior to reaching the treatment site (not shown). In another embodiment, the first and second fluids begin mixing proximate the point P (FIG. 11).

In this manner, embodiments in accordance with the present invention can provide efficient mixing and delivery of the first and second fluids (not shown) to a delivery site (not shown). For example, a mixed activator and base (not shown) can be delivered to a site without clogging concerns. In one embodiment with the base flowing past the activator substantially no clogging can be achieved. In another embodiment, a small "cap" (not shown) is formed at the terminal end 160 of the second orifice 156 after flow of the activator and/or base has ceased. In turn, the small cap of mixed activator and base can be readily removed from the second orifice 156, for example by re-starting flow of the second fluid.

Another advantage can reside in not having to deliver the second fluid at a high enough flow rate or rotational acceleration to produce an atomized flow of the second fluid. In this manner, a relatively small amount of the second fluid can be efficiently delivered without needing to achieve the volumetric flow rates and/or rotational accelerations needed to atomize the second fluid. For example, atomization of the second fluid can be difficult and/or inefficient when delivering the first and second fluids at volumetric ratios greater than 1:1, more difficult and/or inefficient at volumetric ratios greater than or equal to 3:1, and even more difficult at volumetric ratios greater than or equal to 10:1.

In light of the above, embodiments of the present invention overcome at least some problems with spray-type dispensers identified in the Background section of this application by directing the lesser volume fluid into the path of the larger volume fluid via an angled nozzle. For example, embodiments include offset orifices, which deliver a lesser volume fluid distal to a larger volume fluid. In some embodiments, the larger volume fluid is atomized as it exits an orifice and impinges on a second, lesser volume fluid. The lesser volume fluid can be picked up by the larger volume fluid, facilitating improved and adequate mixing of the two fluids prior to reaching a treatment site.

FIGS. 12 and 13 show another embodiment tip element 200 in accordance with the present invention. In one embodiment, the tip element 200 includes a nozzle 202 and a sidewall 204 defining a first orifice 206, a second orifice 208, a first receptacle 210, and a second receptacle 212. The first and second receptacles 210, 212 are configured to receive the first distal projection 116 (FIG. 7) and the second distal projection 118 (FIG. 7) of the connecting element 108 (FIG. 7) as previously described in association with other embodiments.

The first orifice 206 is defined by a sidewall portion 213 and defines volume and extends a length from an origin 214 open to the first receptacle 210 to a terminal end 216. The second orifice 210 is defined by a sidewall portion 217 and also defines a volume and can extend a length from an origin 218 through the nozzle 202 to a terminal end 220. In one embodiment, the terminal end 220 is offset distally to the terminal end 216. In this manner, the first orifice 206 can be "shorter" than the second orifice 208 such that the first and second orifices 206, 208 terminate in a different plane. In one embodiment, the terminal end 220 is distally offset from the terminal end 216 a distance of approximately 0.05 to 0.1 inch, although other dimensions can be equally acceptable.

In one embodiment, the sidewall portions 213, 217, are angled toward one another such that the first and second orifices 206, 208 are defined to extend angularly toward a common point. In this manner, an angled shape of the first and second orifices 206, 208 assist in directing the first and second fluids (not shown) toward each other as they exit the first and second orifices 206, 208, respectively. In one embodiment, the open volume and/or length of the first and second orifices 206, 208 can reduce rotation and flow rate of the first fluid (not shown) and/or the second fluid (not shown) to aid in ensuring that the first and/or second fluids are not atomized. As alluded to above, the nozzle 202 extends distally to emit a second fluid (not shown) downstream of a first fluid. In particular, the first fluid can be dispensed to a point distal from the terminal end 216 to contact a second fluid being dispensed from the terminal end 220 and mix at the terminal end 226 or at a point distal the terminal end 220.

A method of dispensing a first and a second fluid (not shown) from the tip element 200, includes expelling the first fluid from the shorter, first orifice 206 and the second fluid from the longer, the second orifice 208. In one embodiment, the first fluid exits the first orifice 206 and flows over the second orifice 208 where the second fluid is exiting, causing the two liquids to become mixed as they leave the tip element 200. In a related embodiment, both the first and the second fluids are expelled from the first and the second orifices 206, 208, respectively as a drip-type of flow. In another embodiment, both the first and the second fluids are expelled from the first and the second orifices 206, 208, respectively as a stream-type of flow. In yet another embodiment, one of the first and the second fluids is expelled as a drip-type of flow and one of the first and second fluids is expelled as a stream-type of flow.

Several advantages can be achieved with embodiments of the tip element 200. For example, an offset between the terminal ends 216, 220 can help prevent the second fluid (not shown), e.g., an activator, from entering the first orifice 206, otherwise contaminating the first fluid (not shown), e.g., a base, or help prevent the first fluid from entering too far into the second orifice 208, which might otherwise cause undesirable clotting or gelling of the materials. As described, another advantage is the sidewalls 213, 217 can be angled such that the shape of the orifices 206, 208 assist in directing the first and second fluids toward each other, thereby increasing mixing.

In this manner, the tip element 200 should illustrate that orifice "offsetting" can be advantageous for applications where atomization of the fluids (not shown) is not necessary, but instead a bead like application of both fluids is to be applied to a treatment site. As described, an offset can improve mixing without compromising toward clotting or gel formation at the terminal ends 216, 220. Furthermore, while drip flow from both the first and second orifices 206, 208 has been described in association with the tip element 200, it should be noted that in other embodiments, the orifice 208 drips the second fluid while the first orifice 220 atomizes, or sprays the first fluid.

With reference between FIGS. 14 and 15, one embodiment of the connecting element 252 includes a sidewall 256 defining a first chamber 258 and a second chamber 260. In general terms, additional features of the connecting element 252 can be similar to the connecting element 108. The tip element 254 includes a first nozzle 262, a second nozzle 264, and a third nozzle 266. The tip element 254 also defines a first orifice 268, a second orifice 270, a third orifice 272, and a fourth orifice 274. The first, second and third orifices 268, 270, 272 extend through the first, second, and third nozzles 262, 264, 266, respectively. In one embodiment, the fourth orifice 274 can formed to be substantially similar to the first orifice 146 of the tip element 110. By including the first, second, third, and fourth orifices 268, 270, 272, 274, the tip element 254 is configured to facilitate production of atomized and/or non-atomized flow combinations from the first, second, third, and fourth orifices 268, 270, 272, 274 according to the principles and embodiments previously described in association with the tip assembly 22. In one embodiment, the tip element 254 is configured to provide different emission characteristics, or flow types, from the orifices 268, 270, 272, 274, such as drip, stream, or spray.

Upon assembly, the connecting element 252 and the tip element 254 are configured, or otherwise sized, shaped, and arranged to be rotated relative to one another to dispose the first and second chambers 258, 260 "over" the first and third orifices 268, 272. According to this relationship, the tip assembly 250 can dispense a "drip-drip" flow of the first and second fluids (not shown). The connecting element 252 and the tip element 254 can also be rotated to dispose the first chamber 258 "over" the second and fourth orifices 270, 274. According to this relationship, the tip assembly 250 can deliver a "spray-drip" flow of the first and second fluids. From this it should be understood that a user (not shown) can select what combination of flow types (e.g. spray, drip, or stream) is to be applied. Thus, atomized or spray, drip, and stream types of flow are selectively interchanged according to a desire to utilize multiple fluid application modes on a patient without changing between tip assemblies.

FIG. 16 shows another embodiment tip element 300 in accordance with the present invention. In one embodiment, the tip element 300 includes a sidewall 302, an endwall 304, and a nozzle 306 extending from the end wall 304. In general terms, the tip element 300 also has a single orifice 308 extending through the nozzle 306 and the end wall 304.

The sidewall 302 defines a first receptacle (not shown) and a second receptacle (not shown) configured to receive the first and second distal projections 116, 118 (FIG. 7) of the connecting element 108 (FIG. 7) as previously described in association with other embodiments. The orifice 308 defines an origin (not shown) and a terminal end 310, the orifice 308 tapering in width from the origin to the terminal end 310.

The origin (not shown) is open to both the first and the second receptacles (not shown) of the tip element 300. In this manner, upon assembly, the orifice 308 can be in fluid communication with both the first chamber 128 (FIG. 8) and the second chamber 130 (FIG. 8) of the connecting element 108 (FIG. 8). In one embodiment, the pluralities of channels (FIG. 7) associated with the first and second distal projections 116, 118 (FIG. 7) deliver both the first and second fluids (not shown) to the origin of the orifice 308. Rotational acceleration of the fluids and/or the taper of the orifice 308 can facilitate effective mixing of the two fluids within the orifice 308 prior to being delivered from the terminal end 310.

From this, it should be understood that embodiments of the tip element 300 provide advantages in mixing two fluids prior to being delivered from the tip element 300. In particular, this might be desirable in applications where a reaction time of two fluids is extended and earlier mixing is otherwise desirable to decrease reaction time following delivery from the tip element 300.

Figure 17:
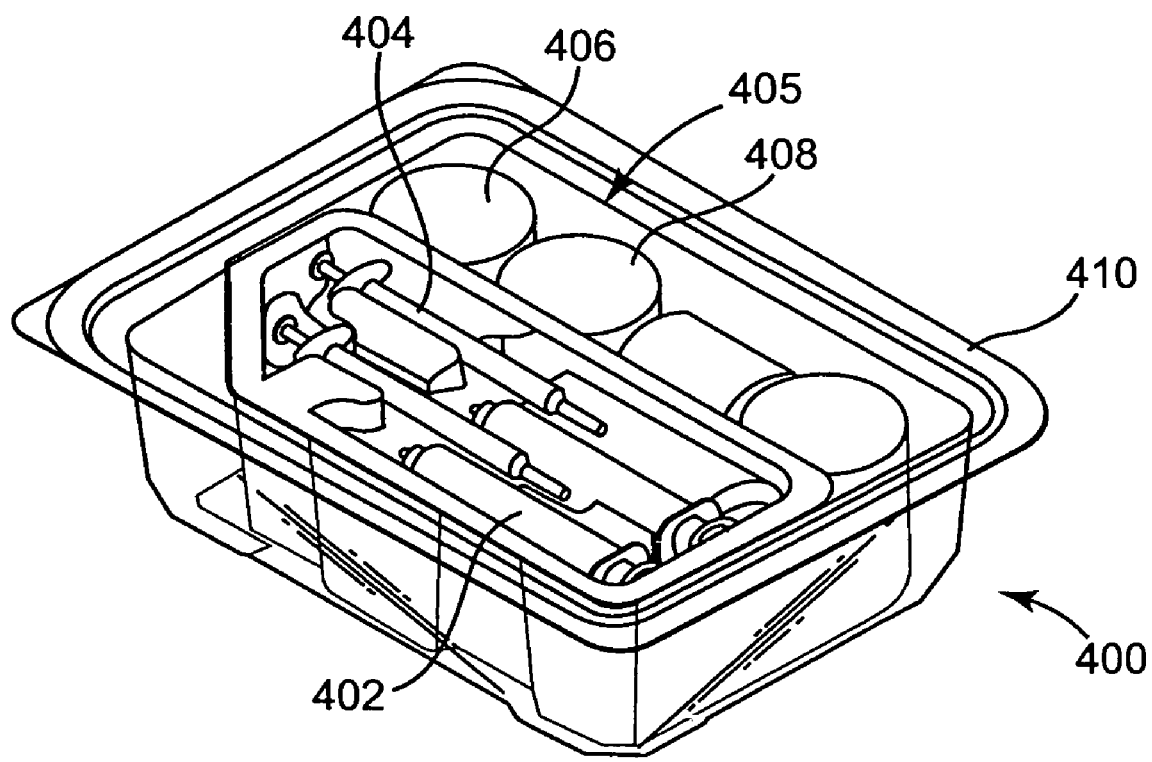
FIG. 17 is a perspective view of one embodiment kit of parts in accordance with the present invention.

One embodiment of a kit of parts 400 associated with the fluid dispensing system 10 is shown in FIG. 17. In one embodiment, the kit of parts 400 includes a first syringe assembly 402, a second syringe assembly 404, a plurality of specimen cups 405 including a first specimen cup 406 and a second specimen cup 408, and a tray 410. The first and second syringe assemblies 402, 404 are similar to embodiments of the first and second syringe assemblies 14, 16 (FIG. 1) as previously described. The plurality of specimen cups 405 can be a type commonly used in such applications.

Figure 18:
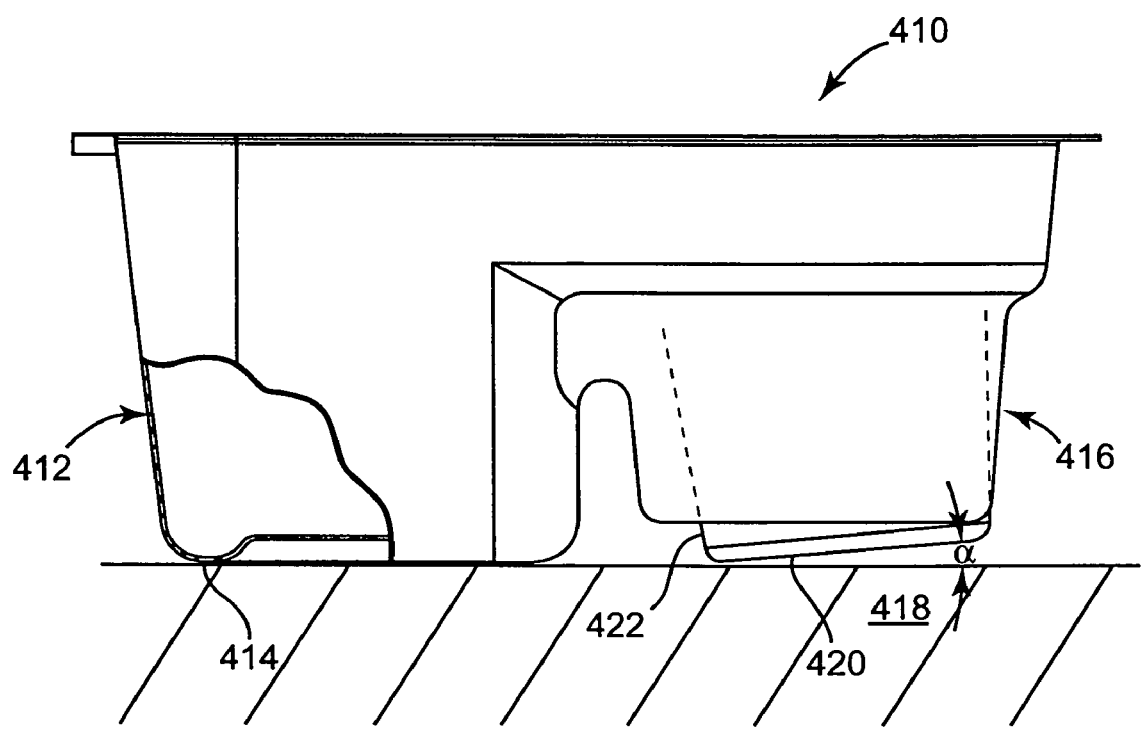
FIG. 18 is a front view of one embodiment tray of the kit of parts of FIG. 17.

The tray 410 is shown in greater detail in FIG. 18. In one embodiment, the tray 410 includes a body 412 defining a bottom support surface 414 and plurality of pockets including a pocket 416. The bottom support surface 414 is configured to support the tray 410 in a horizontal position, for example on a horizontal surface 418. The pocket 416 defines a base 420 and a sidewall 422. The base 420 and the sidewall 422 are configured to maintain the first specimen cup 406 (FIG. 16) in a vertically tipped position as described in greater detail below. The base 420 is offset at an angle α relative to the horizontal position of the tray 410. In one embodiment, the angle α is approximately 5 degrees to approximately 10 degrees, although other dimensions can be equally acceptable.

The first specimen cup 406 (FIG. 17) is placed into the pocket 416 and supported at the angle α. Thus, the first specimen cup 406 can be supported in tipped position relative to the horizontal position of the tray 410. In this manner, the pocket 416 is configured to aid in ease of removing contents of the first specimen cup 406 without requiring manual manipulation of the first specimen cup 406 or the tray 410. For example, it can be necessary to tip the first specimen cut 406 to get a last remaining volume of the first fluid (not shown) from the first specimen cup 406 and into the first syringe assembly 402.

For example, in one embodiment, the first specimen cup 406 is filled with the first fluid (not shown) and the second specimen cup 408 is filled with the second fluid (not shown). A user then draws the first fluid from the first specimen cup 406 as supported in the tipped position using the first syringe assembly 402. In particular, in one embodiment, the user can draw substantially all of the first fluid (not shown) from first specimen cup 402 without having to manually tip the first specimen cup 406 or the tray 410. In a related embodiment, the second specimen cup 408 is maintained in a second pocket (not shown) in a tipped position in a similar manner to that described above. The second specimen cup 408 is filled with the second fluid and the user can draw substantially all of the second fluid from the second specimen cup 408 without having to manually tip the second specimen cup 408 or the tray 410. In another related embodiment, each of the pockets making up the plurality of pockets is configured to hold a corresponding one of the cups 405 in an angled or tipped position.

The tray 410 can be formed from a semi rigid material, such as a polymeric material (e.g., polystyrene, polyester, and PVC). Additionally, other accessories may also optionally be included in embodiments of the kit of parts 400. In one embodiment, the kit of parts 400 includes pluralities of syringe assemblies and specimen cups, clip assemblies (not shown), handle assemblies (not shown), manifold assemblies (not shown), tip assemblies (not shown) and/or other specific procedure-related components. Also, the various embodiment components of the fluid dispensing system 10 (FIG. 1) can be provided in different states of assembly to afford customization or modification to meet the particular desires of a user.

Furthermore, individual elements of embodiments of the kit of parts 400 of the present invention may be packaged together, separately, or in subassemblies depending on a variety of factors such as shelf life and sterilization requirements. They may be assembled at a manufacturing location or at a healthcare location. Any suitable sterilization procedure may be utilized to sterilize the contents of the kit of parts 400. Suitable sterilization techniques include, but are not limited to steam, ethylene oxide, electron beam, vapor (e.g., hydrogen peroxide or peracetic acid), or plasma procedures, for example.

Various advantages can be realized in light of the above-described embodiment kit of parts 400. For example, the difficulties associated with filling syringes with fluids stored in specimen cups can be avoided as described above. In particular, users can avoid having to move specimen cups into a tilted position out of a tray or tip an entire tray.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention. Finally, the words "comprise," "comprising," "defining," "having," "include," "including," and "includes" when used in this specification are intended to specify the presence of stated features, integers, components, or steps, but they do not preclude the presence or addition of one or more other features, integers, components, steps, or groups thereof.

What is claimed is:

1. A method of dispensing two separately maintained fluids to a treatment site of a patient, the method comprising:
    providing a fluid dispensing system including,
        a first syringe assembly maintaining a first fluid,
        a second syringe assembly maintaining a second fluid,
        a tip assembly defining a first orifice and a second orifice, and
        a manifold assembly including,
        a first tube including a flexible body, the first tube in fluid communication with the first syringe and fluidly coupleable to the tip assembly, and
        a second tube including a flexible body, the second tube in fluid communication with the second syringe and fluidly coupleable to the tip assembly;
    cutting the first and second tubes to a desired length;
    fluidly coupling the first tube and the tip assembly, such that the first tube is in fluid communication with the first orifice;
    fluidly coupling the second tube and the tip assembly, such that the second tube is in fluid communication with the second orifice;
    delivering, based on a predetermined volumetric ratio between a volume of the first fluid maintained in the first syringe and a volume of the second fluid maintained in the second syringe, the first fluid from the first syringe assembly, through the first tube, to the first orifice and the second fluid from the second syringe assembly, through the second tube, and to the second orifice.

2. The method of claim 1 further comprising:
    bending the first tube from a first, independently maintained position to a second, independently maintained position.

* * * * *